(12) United States Patent
Ragauskas et al.

(10) Patent No.: US 8,394,025 B2
(45) Date of Patent: Mar. 12, 2013

(54) METHOD AND APPARATUS FOR DETERMINING THE ABSOLUTE VALUE OF INTRACRANIAL PRESSURE

(75) Inventors: Arminas Ragauskas, Kaunas (LT);
Vytautas Petkus, Kaunas (LT);
Romanas Chomskis, Kaunas (LT);
Rolandas Zakelis, Vilkaviskis (LT);
Gediminas Daubaris, Kaunas (LT);
Mark Moehring, Seattle, WA (US);
Eugene A. Saxon, Seattle, WA (US);
Robert Giansiracusa, Bellevue, WA (US); Steve Swedenburg, Kirkland, WA (US); Renaldas Raisutis, Kaunas (LT)

(73) Assignee: UAB Vittamed (LT)

( * ) Notice: Subject to any disclaimer, the term of this patent is extended or adjusted under 35 U.S.C. 154(b) by 498 days.

(21) Appl. No.: 12/492,977

(22) Filed: Jun. 26, 2009

(65) Prior Publication Data
US 2010/0331684 A1    Dec. 30, 2010

(51) Int. Cl.
A61B 8/00     (2006.01)
(52) U.S. Cl. .................. 600/438; 600/437; 600/454
(58) Field of Classification Search .................. 600/437, 600/438, 441, 454
See application file for complete search history.

(56) References Cited

U.S. PATENT DOCUMENTS

| | | | |
|---|---|---|---|
| 4,204,547 A | 5/1980 | Allocca | |
| 4,907,595 A | 3/1990 | Strauss | |
| 4,930,513 A | 6/1990 | Mayo et al. | |
| 4,984,567 A | 1/1991 | Kageyama et al. | |
| 5,016,641 A | 5/1991 | Schwartz | |
| 5,040,540 A | 8/1991 | Sackner | |
| 5,117,835 A | 6/1992 | Mick | |
| 5,606,972 A * | 3/1997 | Routh | 600/455 |
| 5,951,477 A | 9/1999 | Ragauskas et al. | |
| 2002/0062078 A1 | 5/2002 | Crutchfield et al. | |
| 2004/0230124 A1 | 11/2004 | Querfurth | |
| 2005/0096538 A1* | 5/2005 | Chomas et al. | 600/437 |
| 2005/0137479 A1 | 6/2005 | Haider | |
| 2009/0131788 A1* | 5/2009 | Settlemier et al. | 600/438 |
| 2009/0287084 A1 | 11/2009 | Ragauskas et al. | |
| 2010/0249597 A1* | 9/2010 | Shi | 600/454 |

OTHER PUBLICATIONS

Benner et al., "Transcranial Doppler Sonography Pulsatility Index (PI) Reflects Intracranial Pressure (ICP)", 2004, 45-51.*
European Search Report; Application No. EP 10 16 7388; Oct. 22, 2010; 5 pages.
Ragausukas, et al.; "Innovative Non-Invasive Method for Absolute Intracranial Pressure Measurement without Calibration"; ACTA Neurochirurgica (2005) vol. 95; pp. 357-361.
Ragauskas, et al.; "Non-Invasive Assessment of Intracranial Biomechanics of the Human Brain"; Ultragarsas; vol. 63; No. 1; Jan. 1, 2008; 9 pages.

(Continued)

*Primary Examiner* — Brian Casler
*Assistant Examiner* — Christopher Cook
(74) *Attorney, Agent, or Firm* — St. Onge Steward Johnston & Reens LLC

(57) ABSTRACT

A method and apparatus for obtaining the absolute value of intracranial pressure in a non-invasive manner is described by using an ultrasonic Doppler measuring device which detects the intracranial and extracranial blood flow velocities of the intracranial and extracranial segments of the ophthalmic artery. The eye in which the blood flow is monitored is subjected to an external pressure, sufficient to equalize the intracranial and extracranial angle-independent blood flow factors calculated from the intracranial velocity signal and extracranial velocity signal. The absolute value of the intracranial pressure is identified as that external pressure at which such equalization occur

39 Claims, 22 Drawing Sheets

OTHER PUBLICATIONS

Alperin et al., MRI study of cerebral blood flow and CSF flow dynamics in an upright posture: the effect of posture on the intracranial compliance and pressure, Acta Neurochirurgica Supplementum 2005; 95: 177-181.

Alperin et al., Relationship between total cerebral blood flow and ICP measured noninvasively with dynamic MRI technique in healthy subjects, Acta Neurochirurgica Supplementum 2005; 95: 191-193.

* cited by examiner

Software window when apparatus is working in scan mode (adjustment mode). Transducer is positioned in a priori known position that allows us to receive Doppler echo signal from intracranial ophthalmic artery IOA (depth 60...50 mm). Signal from internal carotid artery ICA is seen at depth 72 mm. Transducer rotation angle is 0 degrees.

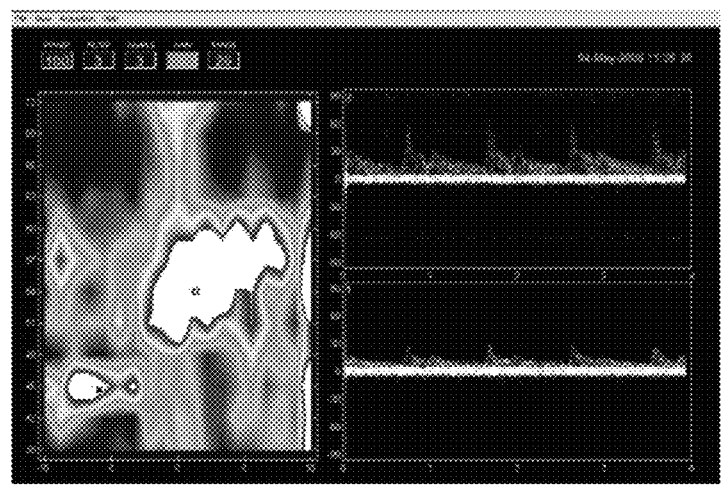

FIG. 7

Software window when apparatus is working in scan mode (adjustment mode). Transducer is rotated by 20 degrees. Both signals from IOA and EOA are seen in left image (depth of IOA signal is 54 mm, depth of EOA signal is 46 mm). Right top image is spectrogram of demodulated Doppler signal of blood flow pulsation in IOA (2 marker) and Right bottom image is spectrogram of demodulated Doppler signal of blood flow pulsation in EOA (2 marker).

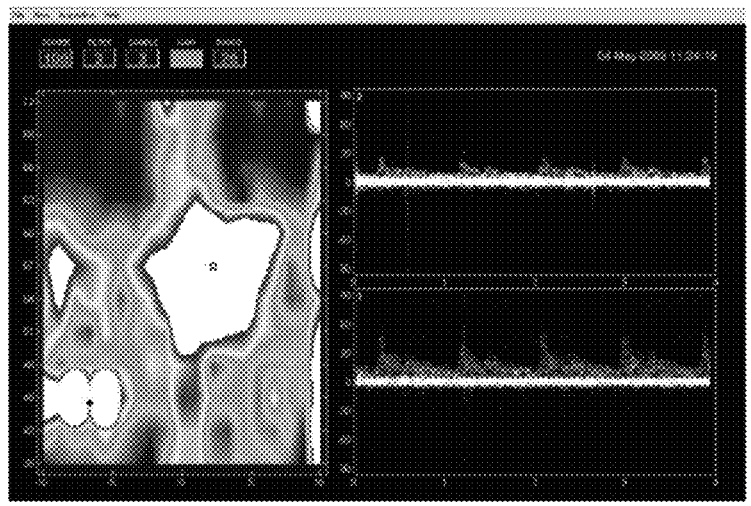

FIG. 8

Software window when apparatus is working in scan mode (adjustment mode). Transducer is rotated by 40 degrees. Both signals from IOA and EOA are seen in left image (depth of IOA signal is 58 mm, depth of EOA signal is 46 mm). Right top image is spectrogram of demodulated Doppler signal of blood flow pulsation in IOA (2 marker) and Right bottom image is spectrogram of demodulated Doppler signal of blood flow pulsation in EOA (2 marker).

Software window when apparatus is working in scan mode (adjustment mode). Transducer is rotated by 60 degrees. Signal from EOA is weak and not suitable for measurements.

Software window when apparatus is working in scan mode (adjustment mode). Transducer is rotated by 120 degrees. Signal from EOA is weak and not suitable for measurements.

Software window when apparatus is working in scan mode (adjustment mode). Transducer is rotated by 210 degrees. Signal from EOA appears and we again have signals simultaneously from IOA and EOA.

Software window when apparatus is working in scan mode (adjustment mode). Transducer is rotated by 230 degrees. Signal from EOA appears and we have again signals simultaneously from IOA and EOA.

Software window when apparatus is working in scan mode (adjustment mode). Transducer is rotated by 260 degrees. Signal from EOA is disappeared gain and therefore is not suitable for measurements.

METHOD AND APPARATUS FOR DETERMINING THE ABSOLUTE VALUE OF INTRACRANIAL PRESSURE

FIELD OF THE INVENTION

The present invention generally relates to a method and apparatus for ultrasonically determining the absolute value of intracranial pressure and more specifically relates to a method and apparatus for determining the intracranial pressure using ultrasonic measurements of the velocity of blood flow through an ophthalmic artery.

BACKGROUND OF THE INVENTION

This invention is an extension and improvement of our previously invented method and apparatus U.S. Pat. No. 5,951,477 for single or single repeatable absolute intracranial pressure (ICP) value measurement and diagnosing of brain pathologies based on such measurements. This document is incorporated by reference in the present application.

An apparatus for determining the pressure and flow inside the ophthalmic artery is described in U.S. Pat. No. 4,907,595 to Strauss. The apparatus uses a rigid chamber that can be affixed and sealed over the human eye so that it can be pressurized to apply an external pressure against the eyeball. An ultrasonic transducer is also mounted to the chamber and oriented to transmit ultrasonic pulses for a Doppler type measurement of the flow inside the ophthalmic artery (OA). The apparatus operates by enabling an operator to increase the pressure to such a level that the blood flow through the OA ceases. The pressure at which this occurs is then an indication of the pressure inside the OA. Typically, the pressure at which this event occurs is in the range of about 170 mmHg.

A problem associated with an apparatus as described in the '595 Patent is that the pressure necessary to obtain the desired measurement is so high that it generally exceeds maximum recommended pressures by a significant amount. When such device is then used for an extended time, tissue damage can arise and may result in an increase in the intracranial pressure, ICP, to unacceptable levels.

Another ultrasonic device for determining changes in intracranial pressure in a patient's skull is described in U.S. Pat. No. 5,117,835 to Mick. Such device involves placing a pair of ultrasonic transducers against the skull and storing received vibration signals. U.S. Pat. No. 4,984,567 to Kageyama et al. describes an apparatus for measuring ICP with an ultrasonic transducer by analyzing the acoustic reflections caused by ultrasonic pulses. Other patents related to ultrasonic measuring of either intracranial pressure or other physiological features are U.S. Pat. No. 4,204,547 to Allocca, U.S. Pat. No. 4,930,513 to Mayo et al., U.S. Pat. No. 5,016,641 to Schwartz, and U.S. Pat. No. 5,040,540 to Sackner.

None of these prior art teachings provide a clear description for obtaining a non-equivocal indication of the absolute value of intracranial pressure (aICP). The measurements tend to be obscured by noise arising from uncertainties in the measurements and by numerous influential factors, such as arterial blood pressure, cerebrovascular autoregulation state, individuality of anatomy, and patient's physiology and pathophysiology. Such influential factors cannot be eliminated by calibration of the "individual patient—non-invasive ICP meter" system because the non-invasive "golden standard" absolute ICP meter does not exist. Thus, there is a need for the capability to derive a measurement of a person's aICP in a safe, accurate and non-invasive manner that can be implemented with reasonable reliability and without the necessity for calibration.

SUMMARY OF THE INVENTION

With an apparatus in accordance with the invention, one can derive an indication of the absolute value of pressure inside a skull (intracranial pressure or ICP) in a non-invasive manner. This indication is obtained using an ultrasonic Doppler measuring technique that is applied through the eye of a person and to the ophthalmic artery (OA) in a safe manner.

This is achieved in accordance with one technique in accordance with the invention, by pressurizing a chamber which is in sealing engagement with a perimeter around an eye, and by using an ultrasonic Doppler measuring device, which is mounted to the chamber, to measure the intracranial and extracranial blood velocities (VI and VE, respectively) of intracranial and extracranial segments of the ophthalmic artery. Velocity parameters representative of or derived from these velocity measurements, VI and VE, are then compared, and the difference between these representative parameters, their difference, $\Delta V$, is identified. $\Delta V$ is then used to control the pressure in the chamber. When the pressure in the chamber causes $\Delta V$ to approach a desired minimum value close to zero, that pressure becomes an indication of the non-invasively derived intracranial pressure (nICP).

The technique of the invention can be implemented in a variety of different manners, such as with a manual increase and control over the pressure to be applied to the chamber while monitoring the parameters representative of intracranial and extracranial velocity signals determined with the ultrasonic Doppler device. When these representative parameters appear substantially the same, the applied pressure at which this occurs is then used to determine the intracranial pressure.

Alternatively, with the ultrasonic Doppler velocity measuring technique of this invention, the ophthalmic artery velocity difference measurement, $\Delta V$, can be used to directly control the pressure in the chamber by applying the signal to a pump. A pressure signal indicative of the pressure in the chamber can be used to store a signal in suitable memory and for display to indicate the nICP.

A further aspect of the invention enables a measurement of the dynamic characteristics of blood flow velocity in the intracranial and extracranial OA segments of which pulsatility is an example but not an exclusive embodiment.

It is, therefore, an object of the invention to provide an apparatus for determining the absolute value intracranial pressure (aICP) using a non-invasive ultrasonic technique (nICP). The aICP value (in mmHg or other pressure units) only can be used for traumatic brain injury or other brain pathology treatment decision making. It was impossible to measure the aICP non-invasively until now.

It is still a further object of the invention to obtain a measurement of the ICP of a patient in a safe and dependable manner.

Another advantage of the invention is the possibility to measure nICP absolute values in the injured and healthy hemispheres of the brain separately using the ophthalmic arteries of both eyes of the patient.

Also, another advantage of the invention is the independence of measurement results from many influential factors such as arterial blood pressure, diameter of the OA, cerebrovascular autoregulation state, and hydrodynamic resistances of the ocular and other distant vessels. The invention achieves this advantage by not using the measured absolute values of blood flow velocities in the intracranial and extracranial OA segments (IOA and EOA respectively). Instead, it uses just the comparison of such velocities or associated pulsatility indices or other parameters of dynamic blood flow to find the "balance point"—the point at which a summary blood flow parameter describing IOA hemodynamics is equal to the summary blood flow parameter describing EOA hemodynamics. It is at the balance point that ICP is equal to the extracranially applied pressure inside the pressure chamber. Such comparison is both accurate and not in need of an independent calibration.

A further advantage of the invention is the ability to make non-invasive absolute ICP value measurements without the necessity to calibrate the "individual patient—non-invasive ICP meter" system. The calibration problem is solved when the proposed method uses the balance of two pressures: ICP and extracranially applied pressure to the human eye and intraorbital tissues. Intracranial and extracranial segments of OA are used as natural "scales" for ICP and extracranial pressure balancing.

A still further advantage of the proposed invention is the high accuracy of non-invasive absolute ICP measurement which is acceptable for clinical practice.

These and other advantages and objects of the invention can be understood from the following description of several embodiments in conjunction with the drawings.

BRIEF DESCRIPTION OF THE DRAWINGS

FIG. 6-13 are plots illustrating the steps of adjusting the ultrasonic transducer in order to get Doppler velocity signals from the IOA and EOA simultaneously. The device of the invention is working in scan mode for these tasks.

DETAILED DESCRIPTION OF THE INVENTION

With an apparatus in accordance with the invention, the ICP inside a person's head can be determined from an observation of the blood velocities inside the OA. This involves an ultrasonic apparatus which senses the response of the blood flow to a pressure "challenge" applied to the tissues around the eye. The pressure challenge is accomplished by a pneumatic or fluid-control device, which can apply a slight pressure to the eye. The pressure is applied to the eye to the necessary level for equilibrating parameters representative of the intracranial and extracranial blood flows in the OA leading to the eye. The possibility of this type of measurement has been demonstrated with the analysis presented in our previous patent U.S. Pat. No. 5,951,477.

Figure 1A:
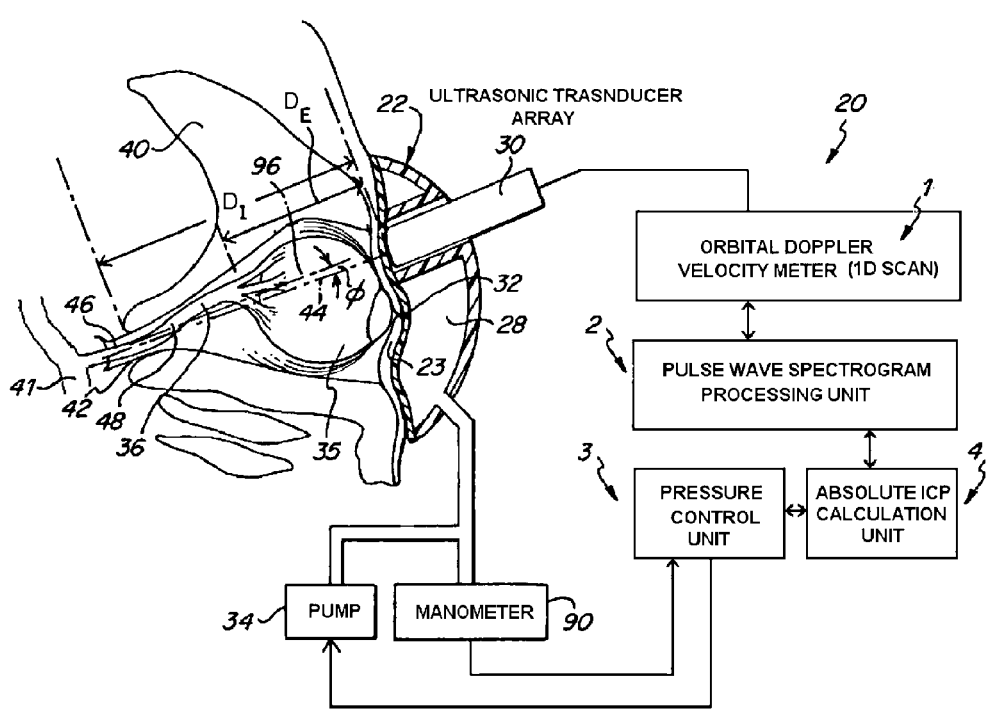
FIG. 1A is a schematic and block diagram illustrating an apparatus with a one-dimensional (1D) scanning ultrasonic transducer array in accordance with the invention.
Figure 1B:
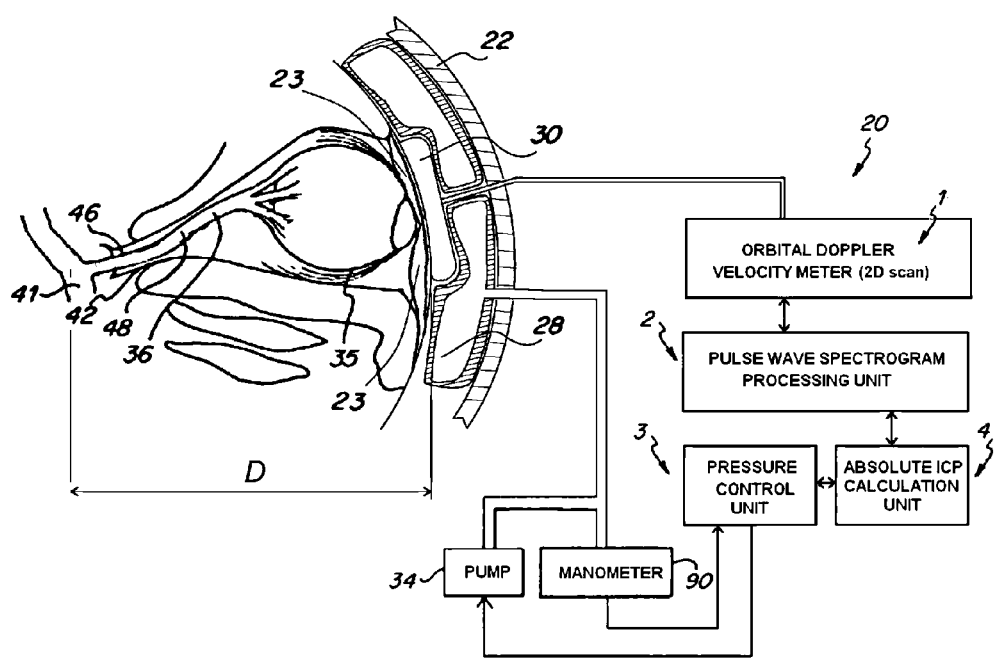
FIG. 1B-1C are schematic views illustrating cases when a concave two-dimensional (2D) ultrasonic transducer array is used.
Figure 1C:
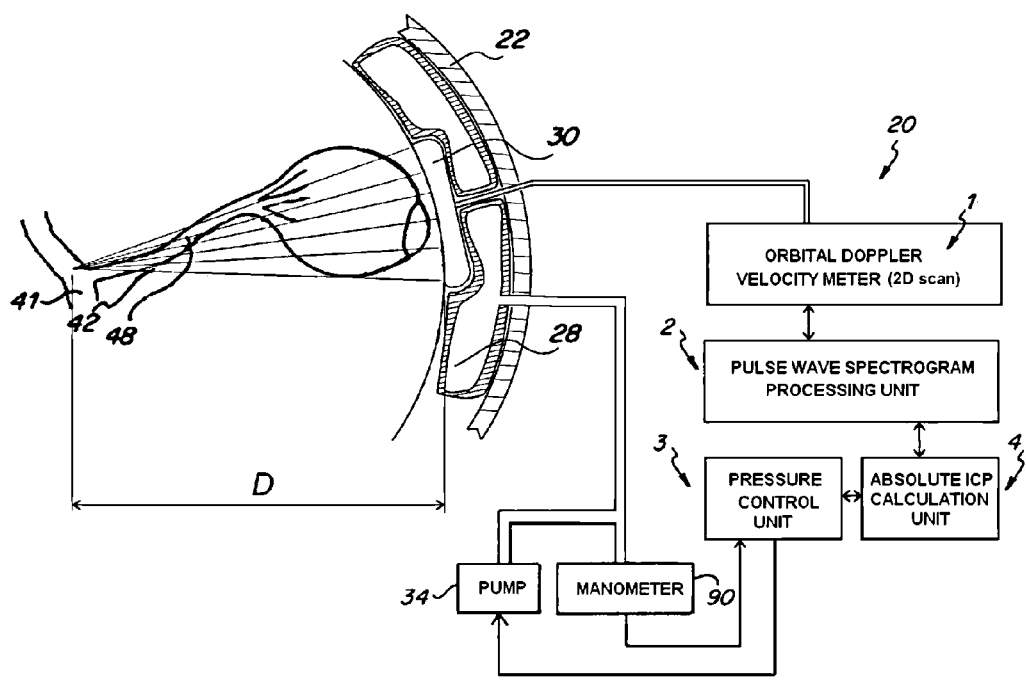
Figure 2:
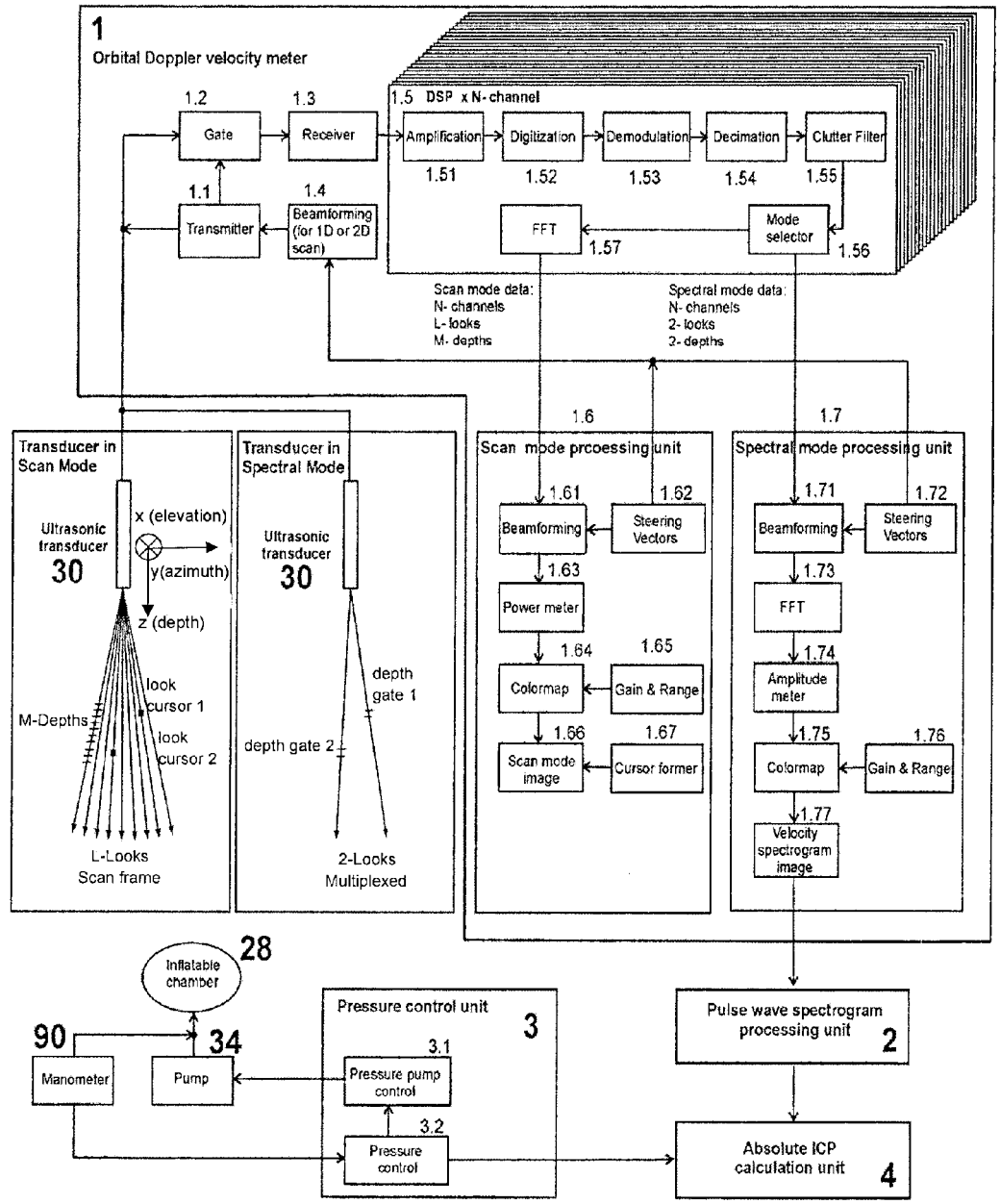
FIG. 2 is a detailed schematic and block diagram view of an apparatus in accordance with the invention.
Figure 3:
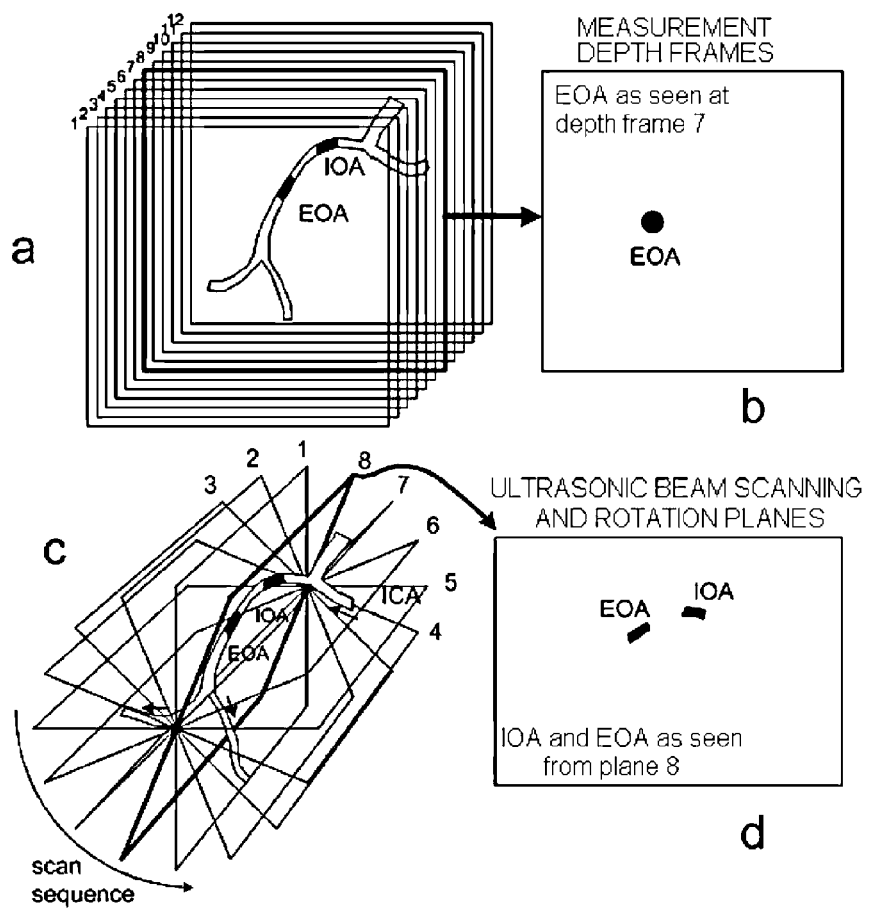
FIG. 3 is a plot illustrating the spatial scan of blood flow velocity in the OA by using an ultrasonic transducer array.
Figure 4A:
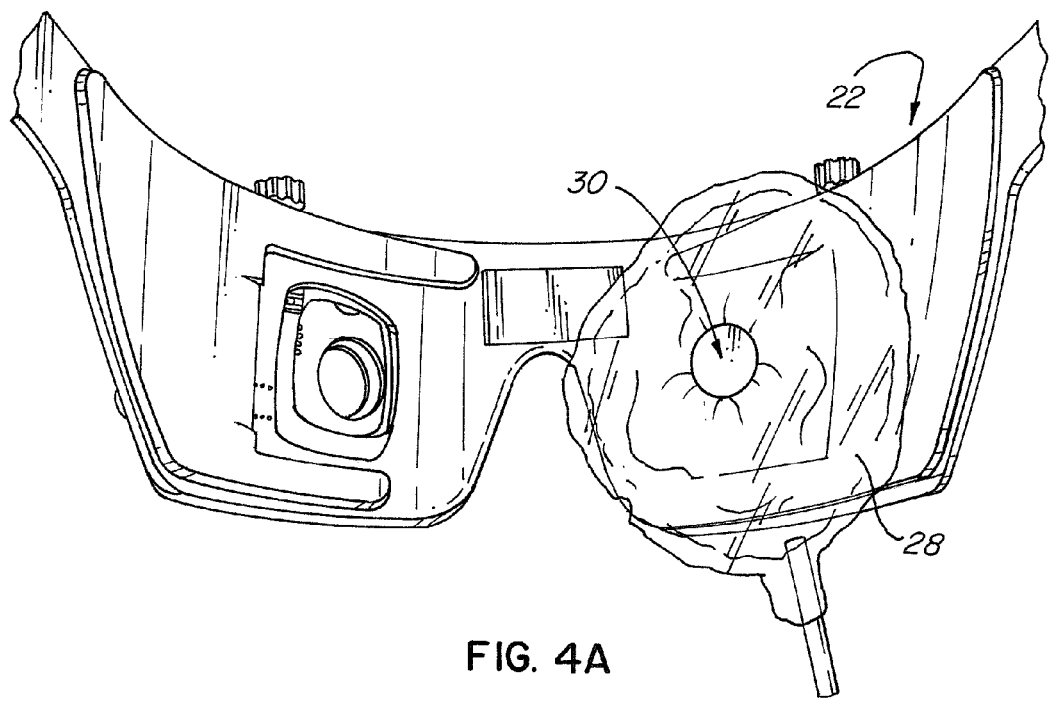
FIG. 4A-4C are perspective views illustrating the mounting of a head frame of the apparatus, in accordance with the invention, to the skull of a patient.
Figure 4B:
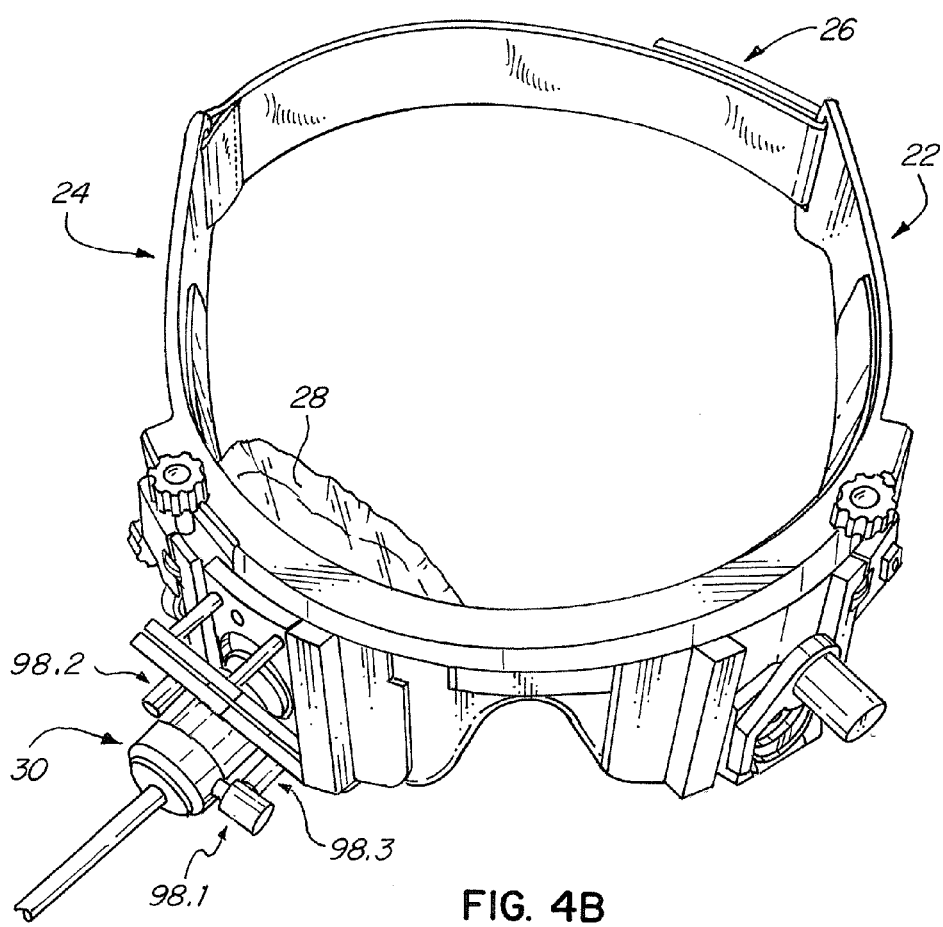
Figure 4C:
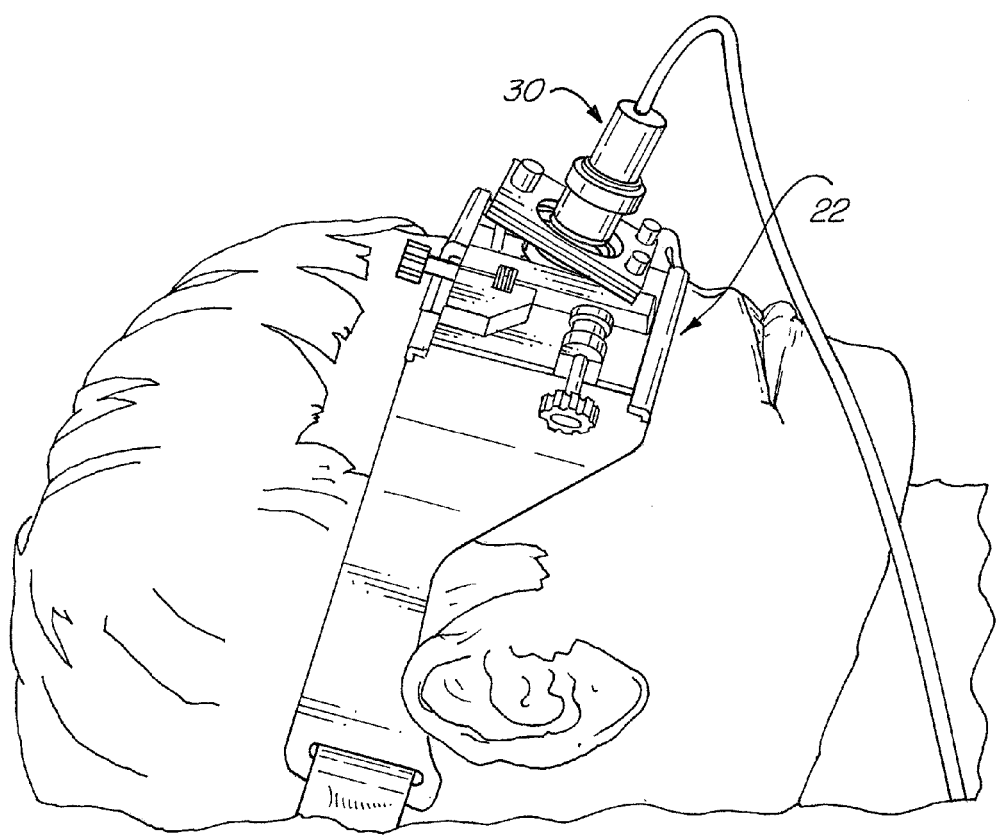

With reference to FIGS. 1, 2, and 3, an apparatus 20 is shown to practice the measurement of the ICP as described above. The head frame 22 of the apparatus is mountable to the head of a person so that an eye engaging inflatable device 28 can apply a slight pressure against the eyelid 23 (FIGS. 4A-4C). Suitable braces and positioning bands 24, 26 are used to hold the head frame 22 in place (FIGS. 4A-4C). The inflatable device is formed of a suitable soft material such as rubber to form an inflatable chamber 28 (FIGS. 4A and 4B). Chamber 28 is approximately annular in shape so as to enable an ultrasonic transducer 30 to be mounted against an inner flexible membrane 32 and enable a pressurization of the chamber by a pump 34 (FIGS. 1A-1C). FIG. 1A shows ultrasonic transducer array 30 which can be a 1D transducer array and can scan electronically the OA in one plane. In FIGS. 1B and 1C, a 2D ultrasonic transducer array 30 is able to perform OA spatial scan in multiple planes. These planes may be parallel or perpendicular to the "boresite" ultrasound beam axis. The distances from the ultrasonic transducer to the internal carotid artery, IOA, and EOA are marked by D, $D_I$ and $D_E$ respectively (FIG. 1A-1C).

The inner flexible membrane 32 conforms to the shape of the eye 35 as illustrated in FIG. 1A and in such manner as to enable the pressure from the inflation of chamber 28 to provide a slight pressurization of the tissues around the eye. These tissues are contiguous with the tissues in the posterior portion of the eye socket, so the applied pressure is effective there as well. This results in a pressurization of the extracranial ophthalmic artery 36. The OA originates from the siphon of the internal carotid artery ICA 41 inside the cranium 40 and passes through the optic nerve canal 42 to the eye 35 (FIGS. 1A-1C).

The preferred embodiment of this invention is shown in FIG. 1 and FIG. 2, and is comprised of an apparatus 20 consisting of: an orbital Doppler velocity meter 1, a pulse wave spectrogram processing unit 2, a pressure control unit 3, and an absolute ICP calculation unit 4.

The orbital Doppler velocity meter 1 controls ultrasonic transducer 30 which can be a 1D transducer array (FIG. 1A) or a 2D transducer array (FIGS. 1B and 1C). This meter has the ability to steer the ultrasound beam relative to the transducer bore site axis. This steering is done electronically within angle ranges from 0 to 8 degrees in one plane for the 1D array embodiment (FIG. 1A) and within a solid angle about the transducer bore site for the 2 D array (FIGS. 1B and 1C). The orbital Doppler velocity meter 1 can work in two modes:

Scan mode (adjustment) is used to search for Doppler velocity signals from IOA and EOA. In this mode, the scan to locate blood flow in the vicinity of the optical canal is done by pointing the ultrasound beam in a series of different directions and sampling the Doppler signal acquired at multiple depths along the beam (each such direction is called a "look" or "look direction"). The look direction is adjusted electronically.

Spectral measurement mode is used when Doppler velocity signals from IOA and EOA have been found and the beam directions ("looks") and depths associated with, respectively, the intracranial and extracranial ophthalmic arteries, are known. In this mode, the transducers are operated in an alternating (pulse by pulse) fashion. This operation is referred to as "multiplexing" the two beam directions and is done in order to receive Doppler velocity signals from the IOA and EOA separately. These signals are then demodulated and used to derive spectrograms characterizing blood flow at the locations of the IOA and EOA.

The orbital Doppler velocity meter 1 consists of: transmitter 1.1, receiver 1.3, beam forming circuit 1.4, digital signal processing DSP N-channels 1.5, and units for data processing in scan mode 1.6 and spectral mode 1.7 (FIG. 2). The beam forming circuit 1.4 can be applied for 1D or 2D scan respectively for cases in FIG. 1A and FIG. 1B.

The transmitter 1.1 generates electrical signals to excite ultrasonic transducer array 30, which can be a 1D or 2D transducer array. Each electrical signal is delayed in beam forming unit 1.4 in order to steer the diagram of ultrasonic transducer at required directions (for 1D or 2D scan). The steering angle is set from steering vectors 1.62 when apparatus 20 is working in scan mode or from steering vectors 1.72 when apparatus 20 is working in spectral mode.

The Receiver 1.3 is put in a low-gain state during transmission of an ultrasonic pulse, and then into a high gain state while listening for echoes. The received signals from each element of ultrasonic transducer array 30 are processed in an N-channel DSP unit 1.5. The number N of DSP channels is equal to the number of elements in the ultrasonic transducer array 30. In DSP channels 1.5, the received signal is sampled in digitization unit 1.52, and demodulated in demodulation unit 1.53 to get a demodulated digital Doppler signal. After demodulation, the signal is decimated with decimation unit 1.54 and filtered with clutter filter 1.55. One skilled in the art will appreciate that digitization, demodulation and decimation are applied to echo data in the "RF" domain, typically across one pulse period, while clutter rejection is applied in the "baseband" domain, across multiple pulse periods. Further, clutter rejection can be applied before or after beam forming, if both are linear processes.

When orbital Doppler velocity meter 1 is working in scan mode, the demodulated and filtered Doppler signal is directed with mode selector 1.56 into FFT unit 1.57 to calculate the spectrum of this signal. In the next steps, this signal is processed in scan mode processing unit 1.6 to reconstruct a spatial image of the Doppler signal intensity distribution in a spatial 3D rendering. In this rendering, the Doppler signal intensity is colored according to signal intensity and plotted based on spatial position. In one embodiment the X-axis is transducer steering angle in degrees while the Y-axis is depth in mm. The color in the image reflects the Doppler signal intensity of blood flow in the eye artery and the spatial location of this artery.

The scan mode processing unit 1.6 consists of: beam forming unit 1.61, steering vectors 1.62, power meter 1.63, Colormap unit 1.64, gain and range control unit 1.65, scan mode image 1.66, and cursor former unit 1.67. With cursor former 1.67, the operator (or the system in an automatic detection mode) is enabled to select and fix two spatial points in the display of the spatial Doppler signal intensity versus spatial position. By placing cursors at the points where Doppler velocity signals indicate blood flow in IOA and EOA, the transducer steering parameters (angle and depth) will be fixed to get Doppler signals only from those selected segments when apparatus 20 is switched in spectral mode. The fixed transducer steering parameters (angle and depth) are then converted into steering vectors 1.72.

When the orbital Doppler velocity meter 1 is working in spectral mode, the transducer steering vectors 1.72 are utilized in a "multiplexed operation"—pulses aimed at the selected segment of the IOA are alternated on a pulse-by-pulse basis with pulses aimed at the selected segment of the EOA. In this mode, the demodulated and filtered Doppler signals from the DSP channels 1.5 are directed with mode selector 1.56 into spectral mode processing unit 1.7. This unit processes only two Doppler signals from the IOA and EOA in order to get velocity spectrogram image 1.77. The spectral mode processing unit 1.7 consists of: beam forming unit 1.71, steering vectors 1.72, FFT calculation unit 1.73, amplitude meter 1.74, Colormap unit 1.75, gain and range control unit 1.76, and velocity spectrogram image unit 1.77.

FIG. 3 illustrates two embodiments for visualization of blood flow signals in the OA with the orbital Doppler velocity meter operating in scan mode. In one embodiment, the ultrasonic transducer 30, which can be a 1D or 2D transducer, performs a scan inclusive of the optical canal, based acquiring Doppler data from a series of different directions ("looks") and depth ranges according to steering vectors 1.62, in order to get a spatial image depicting location of blood flow. Received information regarding the spatial distribution of blood flow can be represented in color maps at different depth frames (FIG. 3a). Each depth frame represents a different distance from the ultrasonic transducer (depth); the color intensity in the depth frame reflects the blood flow signals while the coordinates of the colored spot in the depth frame reflects the transducer steering angle at which the blood flow in the eye artery is detected (FIGS. 3a and 3b). The example in FIG. 3b shows that at fixed depth in frame 7 blood flow is detected in the EOA.

A second embodiment may be used in what may be a simpler technique for simultaneous visualization of blood flow velocity in the IOA and EOA. In this second embodiment, the spatial planes of scanning are made based on rotation of a planar scanning region about the bore site axis of the transducer (FIG. 3c). The rotational method of acquiring the set of scan planes can be implemented by using a 2D transducer array with electronic steering across two spatial angles, or can be implemented with a linear array capable of one scan plane, combined with mechanical rotation of that array. Either method is capable of accomplishing the scan depicted in FIG. 3c. Whichever method is used, the rotation of scanning planes is performed until blood flow velocity signal is detected from both IOA and EOA simultaneously from different depths (FIG. 3d). Note that this technique may be facilitated by first locating the internal carotid artery and manipulating the transducer until the associated flow signal is on the bore site axis, and then performing the rotational scan.

The visual information regarding blood flow spatial distribution may be plotted in a spatial 3D image, or a series of 2D images, but is not restricted to these approaches.

In the eye, blood flow velocities are typically low and difficult to characterize because of poor signal-to-noise ratio (SNR). This is further complicated because ultrasonic Doppler devices as a rule must use very low power in the eye, which contributes to the low SNR. To overcome this disadvantage, the present invention provides significant improvement in SNR of the ophthalmic artery signal by averaging multiple heart cycles after cross-correlation (time) alignment of the set of spectrograms representative of the multiple heart cycles.

The pulse wave spectrogram processing unit 2 performs calculation of a coherently averaged full heart cycle blood flow velocity spectrogram and maximum velocity envelope from the set of spectrograms representative of the multiple heart cycles (FIG. 2). After segmentation of the velocity spectrogram derived from a particular vessel location into separate spectrograms, one for each heart cycle, and synchronization of the heart cycles in these separate spectrograms via maximum-correlation of the Doppler shift signals, the coherent averaging in this step can be applied to obtain the maximum velocity envelope by either taking an average of the synchronized envelopes of the individual heart cycle spectrograms, or the envelope of the average of the synchronized spectrograms. This technique may be included to accomplish significant improvement in the accuracy and resolution of the blood flow maximum velocity envelope.

In order to apply an external pressure on the eyelid, the pressure control unit 3 drives pump 34 and reads data from digital manometer 90 (FIGS. 1A-1C and 2). The absolute ICP calculation unit 4 performs the processing of all measurement data in order to determine the aICP.

The ultrasonic transducer 30 can be a 1D or 2D array transducer from which an ultrasonic beam can be electronically steered in order to enable the system to direct its ultrasonic acoustic pulses concurrently at both intracranial and extracranial segments 46, 48 of the ophthalmic artery 36. Whichever type of transducer, it is helpful that the transducer's central axis, or "bore site", 44, is first aligned to the optical canal and directed to view the IOA 46 and internal carotid artery (ICA) 41 (FIG. 1A). This alignment is accomplished by positioning an ultrasonic transducer on the eyelid according to known a priori information about human skull geometry. The EOA is then found by electronically adjusting the angle of the transducer scan plane. This results in the ability to electronically steer the transducer beam so as to direct its ultrasonic pulses at the intracranial and extracranial segments 46, 48 of the ophthalmic artery 36 (FIGS. 1A-1C). Concurrent observation of blood flow in the intracranial and extracranial ophthalmic arteries is thereby accomplished. The signal location technique described in this paragraph is part of the preferred embodiment for this invention, but one skilled in the art will appreciate that this is one technique to improve signal quality and ease of acquisition, and that the underlying invention is not restricted to its inclusion.

In the operation of apparatus 20, it is desirable that an initial alignment mode be undertaken to assure that the transmitter pulses from the transducer 30 are properly directed at both the intracranial and extracranial segments 46, 48 of the ophthalmic artery 36 (FIGS. 1A-1C). This involves adjustments in the angle phi between the bore site axis 44 of the ultrasonic transducer 30 and the alignment axis 96 of the ophthalmic artery passage 42 (FIG. 1A). Such adjustment can be done with the alignment screws 98.1, 98.2 and 98.3 or with such other suitable frame affixed between the band 26 and the transducer 30 in FIG. 4.

As described above, one advantage of the present invention is the independence of measurement results from many influential factors such as arterial blood pressure, diameter of the OA, cerebrovascular autoregulation state, and hydrodynamic resistances of the ocular and other distant vessels. A unique and critical advantage of the invention is the ability to make non-invasive absolute ICP value measurements without the necessity to calibrate the non-invasive ICP meter system. The invention achieves these advantages by not using the measured absolute values of blood flow velocities in the intracranial and extracranial OA segments (IOA and EOA respectively). Instead, it uses just the comparison of such velocities or associated pulsatility indices or other parameters representative of blood flow dynamics, to find the "balance point"—the point at which a summary blood flow parameter describing IOA hemodynamics is equal to the summary blood flow parameter describing EOA hemodynamics. At the balance point, the ICP is determined and is equal to the extracranially applied pressure inside the pressure chamber. Such comparison is accurate and independent of the influential factors noted above since it is always find this balance point regardless of these factors.

A necessary property of the parameters representative of blood flow dynamics above is that they are independent of different angles at which Doppler blood flow velocities are measured in the IOA and EOA. Therefore when the blood flow pulsation parameters are measured, angle-independent blood flow factors are calculated. In one embodiment, these blood flow pulsation parameters are peak systolic velocity (VS) and end diastolic velocity (VD). Other measurement points of the blood flow envelope within one heart cycle may be used to calculate an angle-independent blood flow factor. The angle-independent blood flow factor in one embodiment is the pulsatility index, which is calculated for measurements in IOA and EOA:

$$PI_{IOA}=2*(VS_{IOA}-VD_{IOA})/(VS_{IOA}+VD_{IOA}),$$

$$PI_{EOA}=2*(VS_{EOA}-VD_{EOA})/(VS_{EOA}+VD_{EOA}).$$

One skilled in the art will appreciate that any other index of blood flow velocity pulsation which is not influenced by the OA insonation angle can also be used (e.g., resistivity index, any non-standard index which uses more than two measurement points of the blood flow envelope within one heart pulse, etc.).

The "balance point" noted above, at which parameters representative of blood flow are equal in the EOA and the IOA, is accomplished when:

$$PI_{IOA}=PI_{EOA},$$

or $$PI_{IOA}/PI_{EOA}=1.$$

Pulsatility index is a highly vulnerable metric in that it takes two points out of an entire cardiac cycle of information—velocity envelope values at peak systole and diastole—and constructs an index. Using averaged heart cycle blood flow velocity spectrograms (as described above) greatly reduced the uncertainty associated with each of these two points. Due to the improvement in accuracy and precision of the envelope function from using the averaged heart cycle spectrograms, the calculation of the pulsatility index as used in the ICP determination is in turn of higher accuracy and precision.

Figure 5:
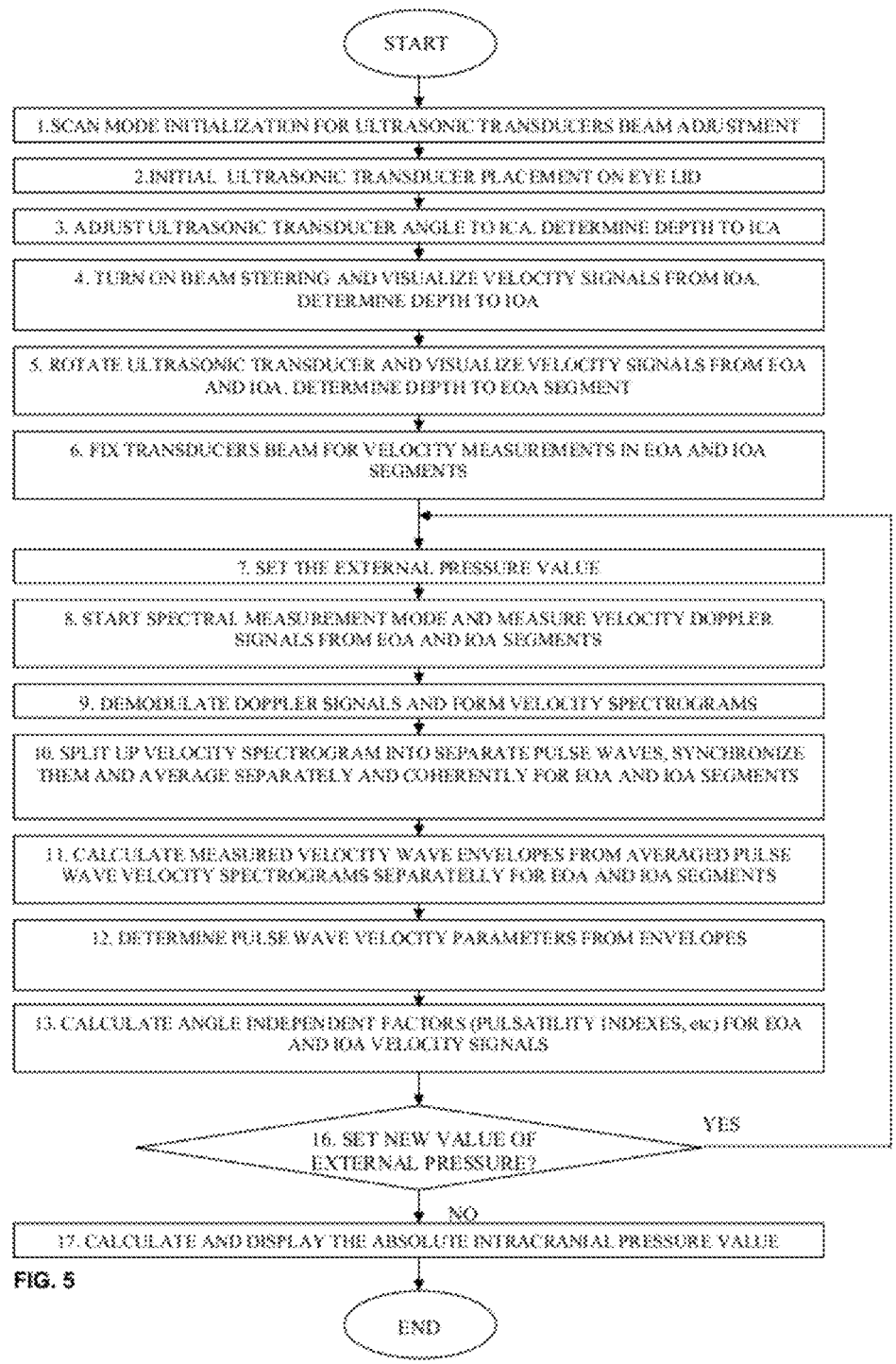
FIG. 5 is a flow chart for a method of using the apparatus shown in FIG. 1A-1C for measuring the absolute value of intracranial pressure.

The flow chart of apparatus 20 with reference to FIGS. 1, 2, 3 and 4 is shown in FIG. 5.

The steps to measure non-invasive intracranial pressure (nICP) are now enumerated. There are two primary aspects to this measurement: scan mode and spectral mode. Scan mode is comprised of steps #1-6 below, and spectral mode is comprised of the remaining steps.

Step #1: Software initialization of scan mode. This mode allows for the operator to align the ultrasonic transducer in the following sequence.

Step #2: Head frame with ultrasonic transducer is placed on patient and acoustic contact between ultrasonic transducer and eyelid is established with coupling gel or acoustically similar material.

Figure 6:
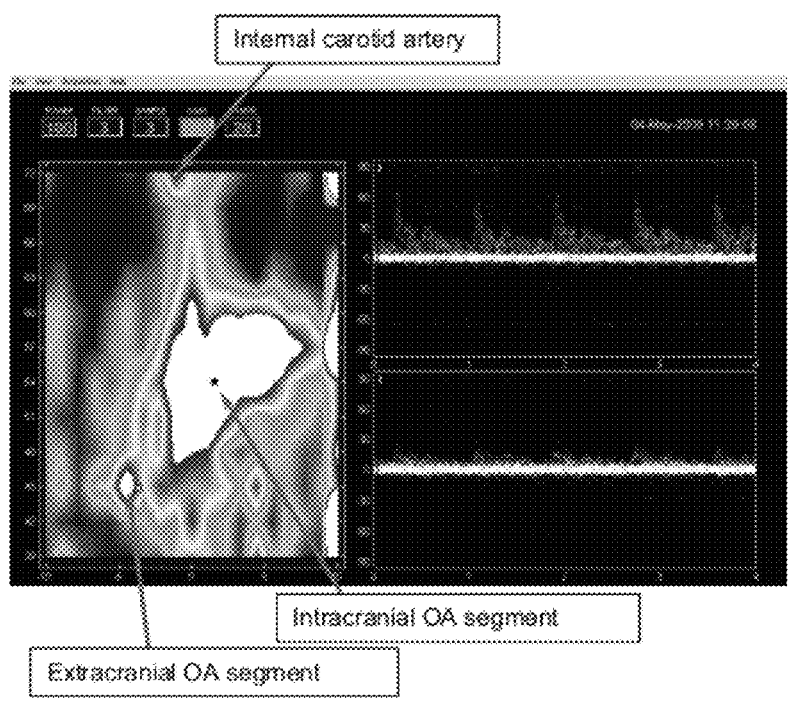

Step #3: Transducer is fixed in the head frame according to a priori known angles and positions that align the transducer central axis to the optical canal. This alignment is most successful when the blood flow signal can be observed in the internal carotid artery, ICA. The distance between the ultrasonic transducer to ICA is a priori known to be in range of depth from 65-75 mm (FIG. 6).

Step #4: The steering of the ultrasonic transducer is manipulated in order to visualize the blood flow signal from the IOA. The depth of the IOA signal is between 5 and 6 mm less than the distance from transducer to the ICA (FIG. 6).

Step #5: For a 1D transducer, it is rotated around its axis until the signal from EOA appears. The depth of the EOA is approximately 5 to 7 mm less than the distance from transducer to the IOA. Both signals from the intracranial and extracranial segments of ophthalmic artery (IOA, EOA) must be clearly seen in the software window while in scan mode (FIGS. 7-13). If the 2D array embodiment is utilized, then the manual steering described above can be accomplished electronically.

Figures FIG. 6-13 show the software windows when the apparatus is working in scan mode (also known as adjustment mode) and the transducer is rotated around its axis:

In FIG. 6, the transducer rotation angle is 0 degrees at which the velocity Doppler signal from the ICA is seen at depth ~72 mm and the signal from the IOA is seen at depth ~50-60 mm, as shown in the left image.

In FIGS. 7-8, the transducer rotation angles are 20 and 40 degrees, respectively, at which the velocity Doppler signals are seen simultaneously from the IOA and EOA in the left image: IOA (depth ~54 mm) and EOA (depth ~46 mm).

Figure 9:
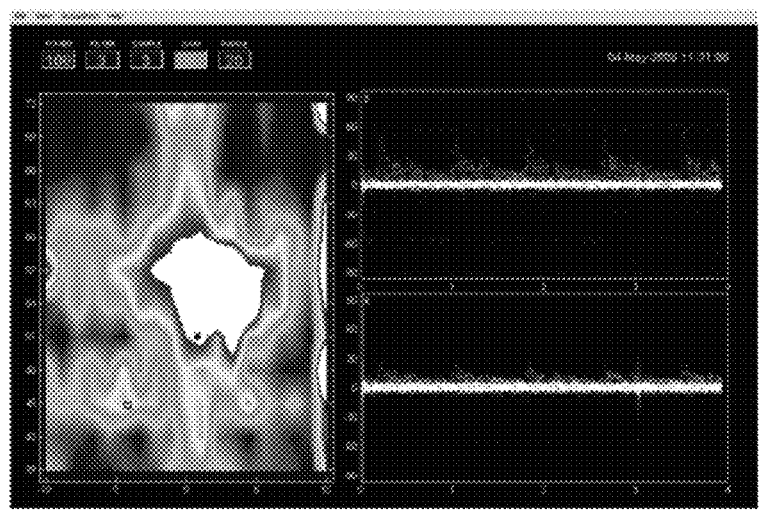
Figure 10:
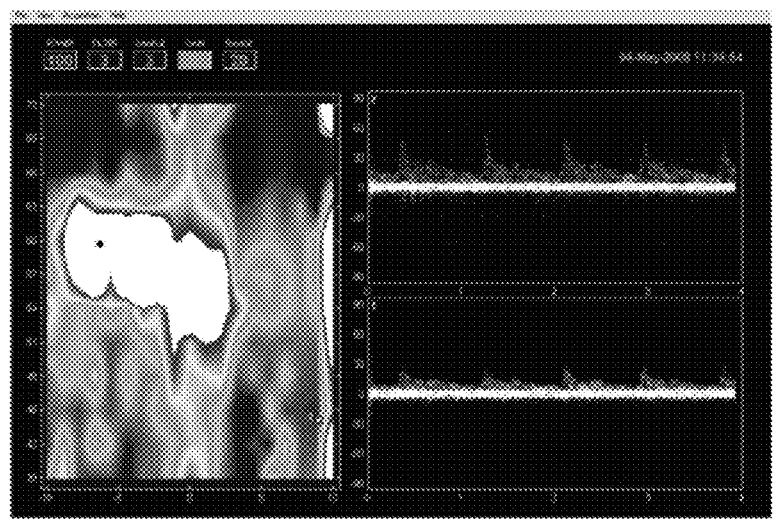

In FIGS. 9-10, the transducer rotation angles are 60 and 120 degrees, respectively, at which the only velocity Doppler signals seen are from the IOA (depth ~54 mm). The signal from the EOA is weak and unsuitable for measurement.

Figure 11:
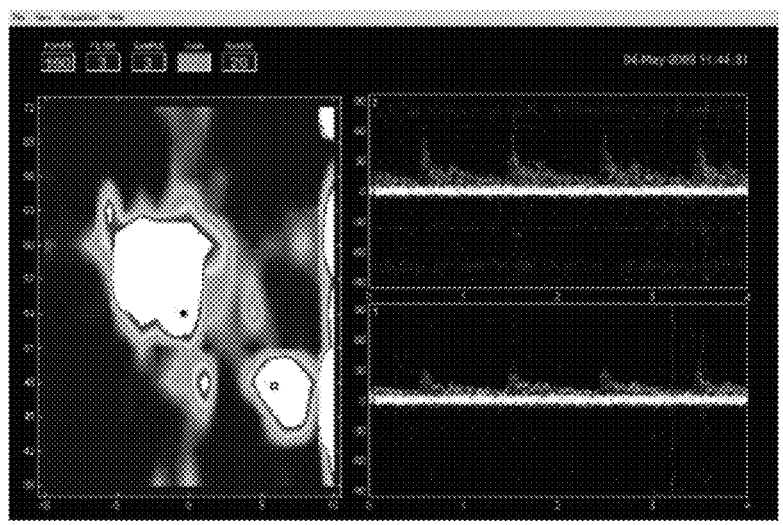
Figure 12:
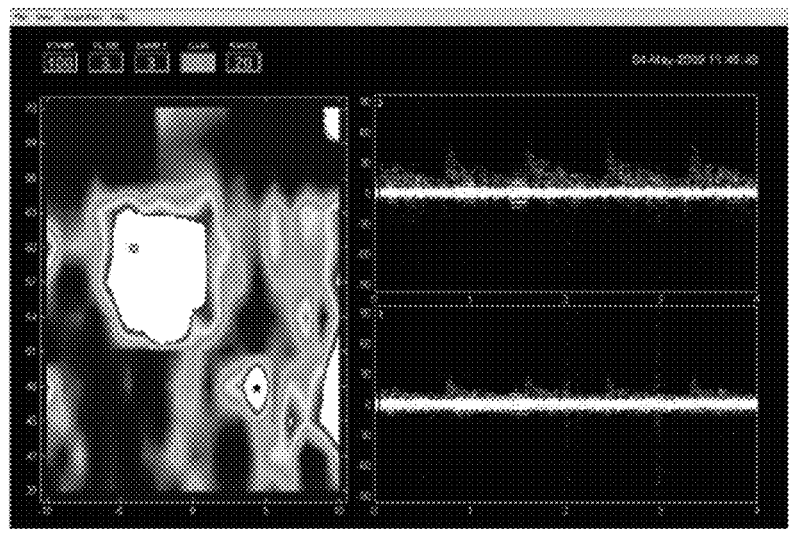

In FIGS. 11-12, the transducer rotation angles are 210 and 230 degrees, respectively, at which the velocity Doppler signals are seen again from the IOA and EOA in left the image: IOA (depth ~54-60 mm) and EOA (~45-48 mm).

Figure 13:
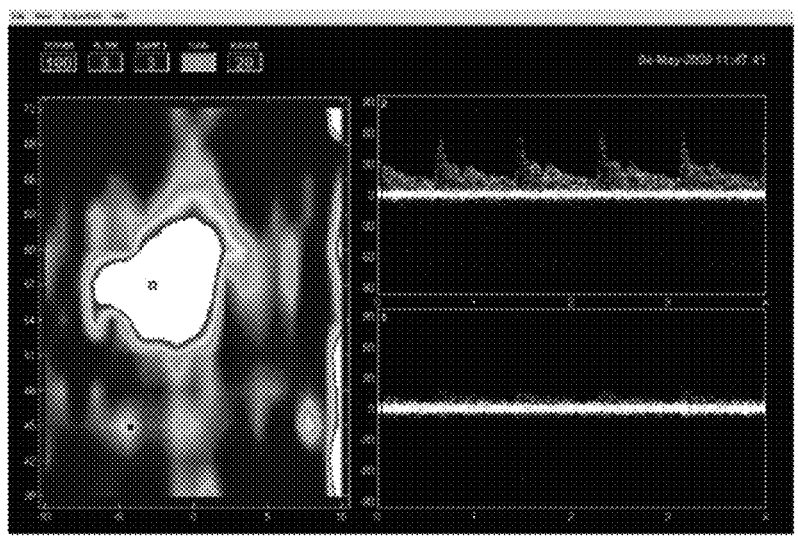

In FIG. 13, the transducer rotation angle is 260 degrees at which the velocity Doppler signals are seen only from the IOA (depth ~54 mm). The signal from the EOA is again weak and unsuitable for measurement.

In scan mode FIGS. 6-13, the Doppler echo signals shown are obtained by systematically steering the ultrasound beam in a B-mode style planar region. Note that in the images on the left, the Y-axis is depth in mm, and the X-axis is the transducer steering angle in degrees. The spectral mode signals are shown in the images on the right; the top and bottom right images are Doppler velocity signals from locations designated by markers 2 and 1 respectively (in m/s). The markers are located in the scan mode image on the left.

In FIGS. 6-13, it is shown that by turning the ultrasonic transducer around its axis, we always obtain a signal from the IOA. This means that an a priori angle and position of the transducer's positioning is set properly and confirmed empirically (i.e., the transducer central axis is aligned to the optical nerve canal). The signal from the EOA appears only at angles 20-40 degrees and 210-230 degrees. This is consistent with the fact that rotation of the scan plane by 180 degrees will produce the same scan plane.

Step #6: The angles and depths at which selections are made for sampling velocity Doppler signals (spectral mode on the right side of these images) are fixed by manually placing markers in the software window—by pointing and clicking the mouse—when the apparatus is working in scan mode (adjustment).

After the transducer is positioned to obtain velocity Doppler signals from two different depths and directions ("looks"), the apparatus is put in measurement mode, also referred to as "spectral mode", in which the transducer is working by alternating its pulsing activity on a pulse-by-pulse basis between two fixed angular steering directions. In the next series of steps #7-14 are the procedures for measuring absolute value of intracranial pressure.

Step #7: A known external pressure on eyelid is applied by inflating pressure chamber 28 by pump 34 (FIGS. 1A-1C and 2). Using manometer 90, the pressure within chamber 28 is measured and used by the apparatus software to control pump 34. The measured pressure value is transferred from manometer 90 and stored for each measurement cycle (pressure is varied across measurement cycles).

Step #8: When required pressure is set and stabilized, the software makes Doppler spectral measurements in which the velocity signals are collected and analyzed from the IOA and EOA segment locations.

Step #9: Doppler velocity signals measured in the IOA and EOA segments are demodulated and used to form a spectrogram representative of blood flow at each location.

Figure 14:
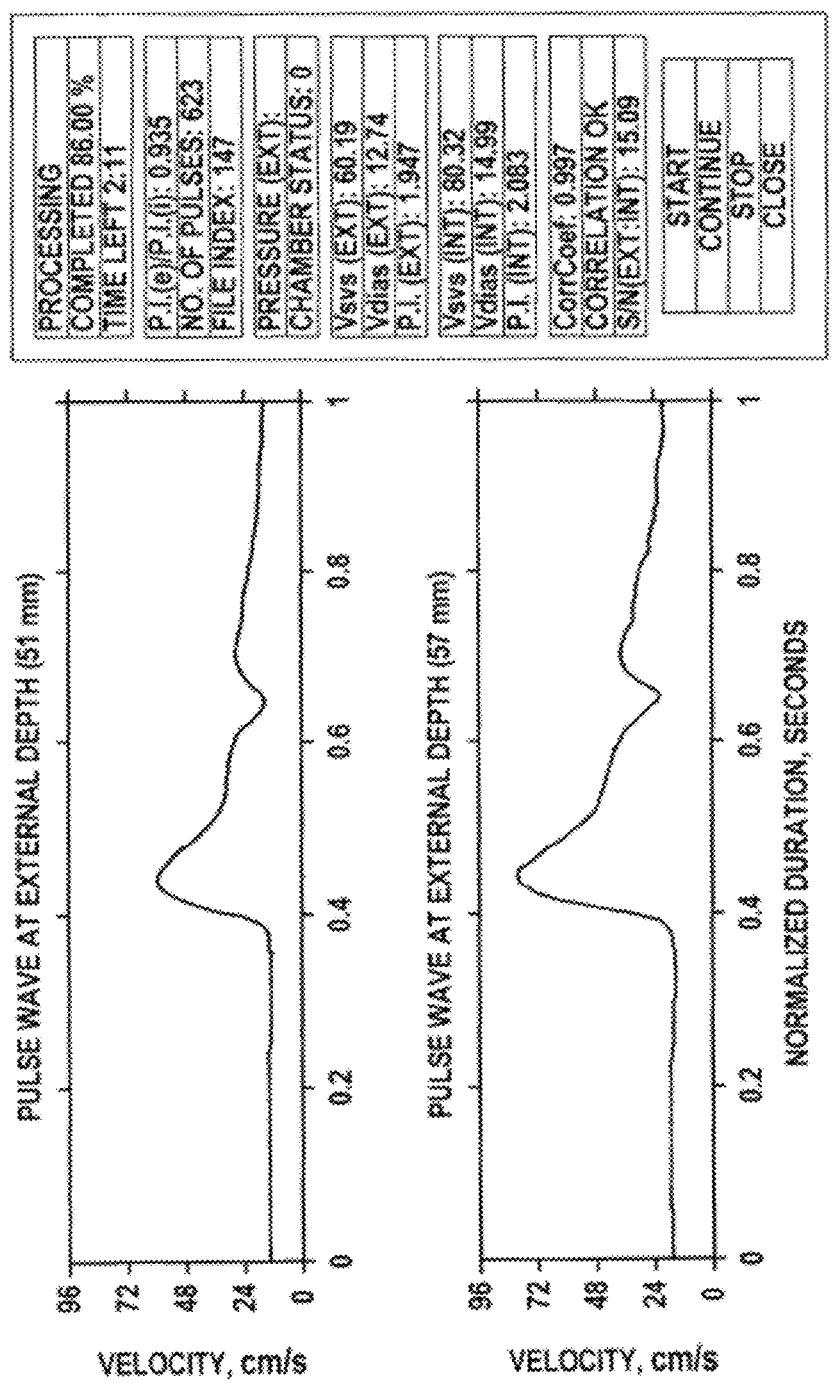
FIG. 14 is a view of the software window that shows the procedures of averaging the spectrogram across multiple heart cycles from the IOA and EOA simultaneously. The device of the invention is working in spectral measurement mode for this task.

Step #10: Spectrograms of velocity signals at the IOA and EOA locations are parsed into separate heart cycles, which are synchronized and coherently averaged to form a separate IOA composite heart cycle spectrogram and an EOA composite heart cycle spectrogram (FIG. 14).

Step #11: The peak velocity envelopes for IOA and EOA composite heart cycle spectrograms are calculated (FIG. 14).

Step #12: The parameters representative of velocity signals in the composite heart cycle spectrograms of the IOA and EOA (VS for peak systolic velocity and VD for end diastolic velocity) are calculated from maximum flow velocity envelopes derived from these composite spectrograms.

Step #13: Angle independent factors such as pulsatility indexes are calculated from measured velocity signals separately for IOA and EOA composite spectrograms.

Step #14: The algorithm now repeats measurements of angle independent factors at different pressures applied to the eye by performing steps #7-13 for each different externally applied pressure. The externally applied pressure varies by adjusting the inflation pressure of the chamber placed adjacent to the eye. The external pressure is changed within desired range by increasing it, for example, from 0 mmHg to 30 mmHg in increments such as 5 mmHg. At each fixed pressure, the measured velocity parameters in the IOA and EOA are stored for further processing.

Figure 15:
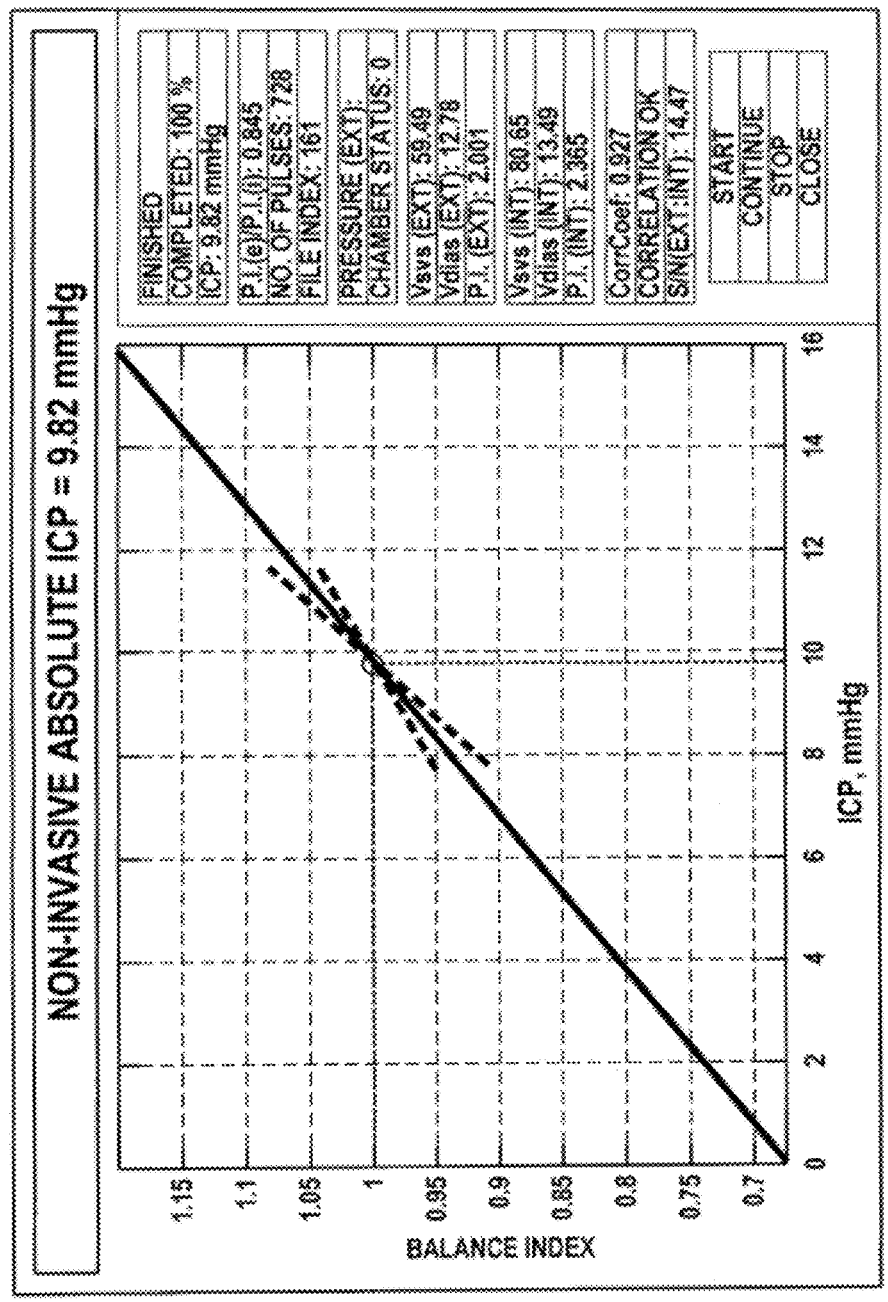
FIG. 15 is a view of the software window that shows the procedures for the calculation of aICP according to the measured data and to the method of the invention.

Step #15: When the measurement of velocity parameters in the IOA and EOA is completed, the calculation of aICP is performed. The ICP is the pressure that achieves the "balanced point" where the calculated parameter representative of IOA blood flow is equal to the calculated parameter representative of EOA blood flow (FIG. 15).

Figure 16:
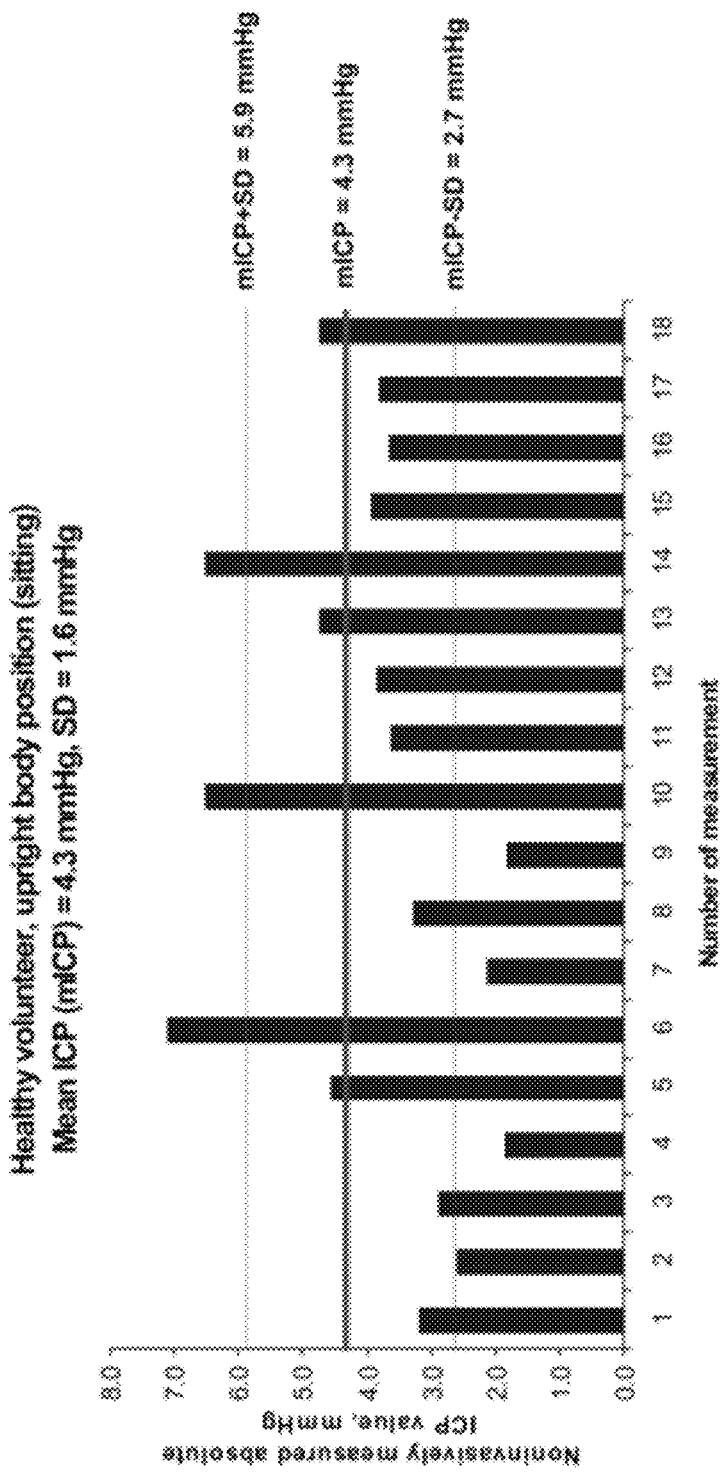
FIG. 16 is a plot illustrating the results of serial non-invasive aICP measurements of the same healthy volunteer obtained with an apparatus in accordance with the invention.

The result of non-invasive absolute ICP value measurements with an apparatus in accordance with the invention is shown in FIG. 16. Serial non-invasive absolute ICP value measurements have been performed on the same healthy volunteer. The measurements are conducted with 15 minute breaks between two consequent measurements. The conclusion is that the standard deviation (SD=1.7 mmHg) is very low and is interpretable as a physiological variance of aICP combined with the absolute error of non-invasive absolute ICP measurement. The absolute error of ICP measurement is lower than +/−2.0 mmHg (FIG. 16). The error +/−2.0 mmHg is a nominal error of existing invasive absolute ICP meters.

Figure 17:
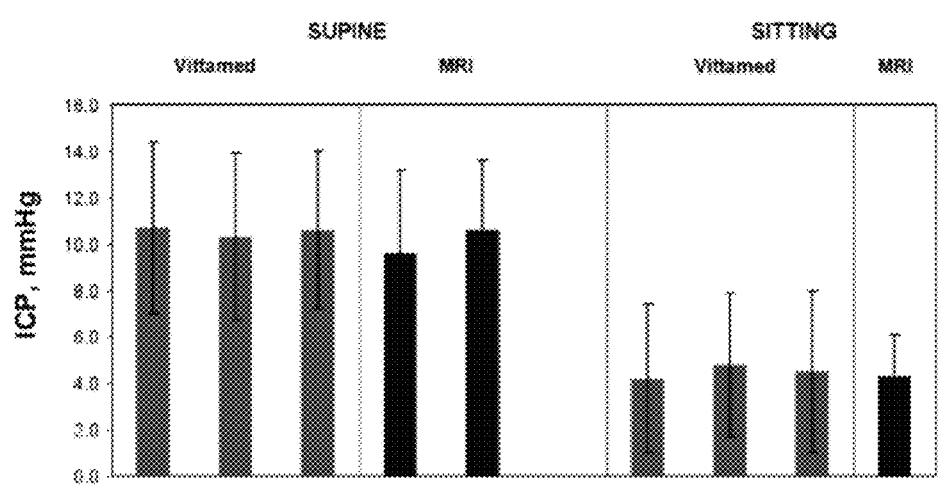
FIG. 17 shows the comparison of non-invasive aICP measurement results obtained with a phase contrast MRI apparatus (See Alperin et al., MRI study of cerebral blood flow and CSF flow dynamics in an upright posture: the effect of posture on the intracranial compliance and pressure, Acta Neurochirurgica Supplementum 2005; 95: 177-181; Alperin et al., Relationship between total cerebral blood flow and ICP measured noninvasively with dynamic MRI technique in healthy subjects, Acta Neurochirurgica Supplementum 2005; 95: 191-193) and with apparatus in accordance with the invention. These results also are listed in Table 1 below.

In FIG. 17, non-invasive absolute ICP measurement results obtained using phase contrast MRI apparatus (See Alperin et al., MRI study of cerebral blood flow and CSF flow dynamics in an upright posture: the effect of posture on the intracranial compliance and pressure, *Acta Neurochirurgica Supplementum* 2005; 95: 177-181; Alperin et al., Relationship between total cerebral blood flow and ICP measured noninvasively with dynamic MRI technique in healthy subjects, *Acta Neurochirurgica Supplementum* 2005; 95: 191-193) are compared with results obtained using an apparatus in accordance with the invention on a group of healthy volunteers. Forty-two healthy volunteers were studied in supine and sitting body positions using a proposed apparatus. Three different ways of transcranial Doppler (TCD) signal analysis were used. These results are also listed in Table 1 below. The good agreement between experimental aICP measurement data using MRI and data using the proposed apparatus is evidence that the proposed method and apparatus are of high accuracy and do not require calibration.

TABLE 1

| POSITION | MRI | | Vittamed | |
|---|---|---|---|---|
| | Mean ICP, mmHg | SD, mmHg | Mean ICP, mmHg | SD, mmHg |
| SUPINE | 9.6 | 3.6 | 10.7 | 3.7 |
| | 10.6 | 3.0 | 10.3 | 3.6 |
| | | | 10.6 | 3.4 |
| SITTING | 4.5 | 1.8 | 4.2 | 3.2 |
| | | | 4.8 | 3.1 |
| | | | 4.5 | 3.5 |

FIG. 18 shows the measured typical dependence of the pulsatility index in the IOA and EOA of the ophthalmic artery. The measurements were performed with the apparatus in accordance with the invention on healthy volunteers in a supine body position for which normal aICP is close to 10 mmHg (see Table 1).

Figure 18A:
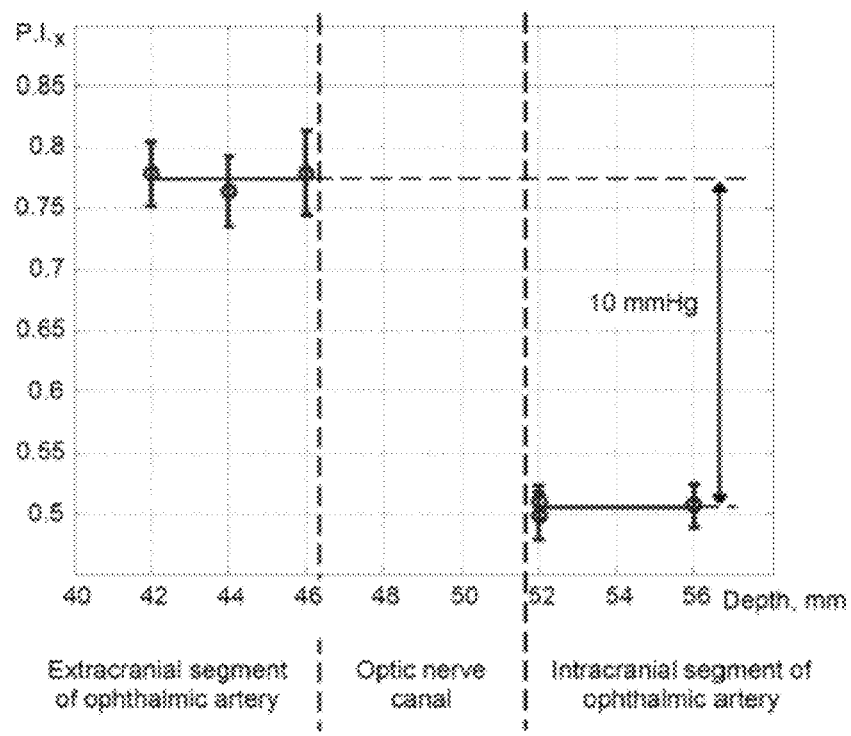
FIG. 18A-18B show measured typical dependence of the pulsatility index in OA on the measurement depth with an apparatus in accordance with the invention, without and with, respectively, an external pressure applied to the eye.
Figure 18B:
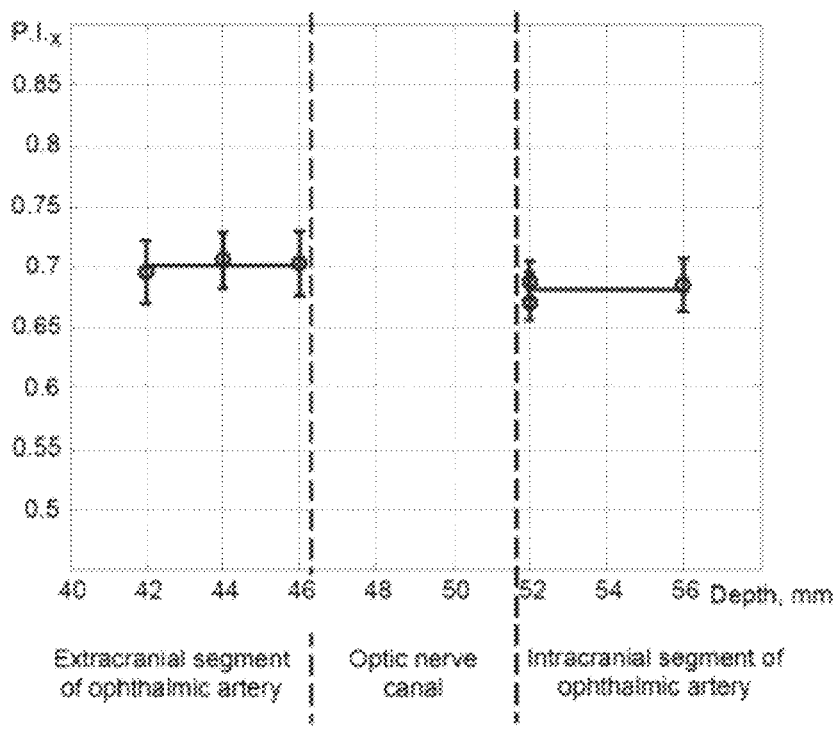

FIG. 18A shows the mean value and standard deviation of measured pulsatility indexes in the IOA and EOA when the external pressure applied in the pressure chamber (Pe) is 0 mmHg. FIG. 18B also shows the same parameters when Pe is 10 mmHg and when Pe≈aICP.

The experimental results shown in FIG. 18 are evidence that the achievable uncertainty U of aICP measurement by proposed method and apparatus is low enough (U<+/−2.0 mmHg) and acceptable for different clinical applications.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. An apparatus for non-invasively determining the absolute value of intracranial pressure of a living body comprising:
   a Doppler device for noninvasively sensing blood flow in an ophthalmic artery extending from inside the cranium into an eye of the living body;
   a steering device for electronically directing ultrasonic pulses generated by said Doppler device at a plurality of depths and a plurality of steering angles in a plurality of planes passing through a central axis of said Doppler device;
   said Doppler device being adapted to receive said ultrasonic pulses from said plurality of depths and said plurality of steering angles in said plurality of planes passing through a central axis of the Doppler device and generate a Doppler signal representative thereof;
   a scan-mode processing unit adapted to receive said Doppler signal and noninvasively locate an intracranial segment of said ophthalmic artery and an extracranial segment of said ophthalmic artery;
   said scan-mode processing unit further adapted to select an intracranial steering parameter representative of a steering angle and a depth corresponding to said intracranial segment of the ophthalmic artery and select an extracranial steering parameter representative of a steering angle and a depth corresponding to said extracranial segment of the ophthalmic artery and generate an intracranial steering vector and an extracranial steering vector from said intracranial steering parameter and extracranial steering parameter, respectively;
   a multiplexer for directing said ultrasonic pulses in an alternating fashion at said intracranial segment of the ophthalmic artery and said extracranial segment of the ophthalmic artery according to said intracranial steering vector and said extracranial steering vector, respectively;
   a spectral-mode processing unit adapted to concurrently generate intracranial velocity and extracranial velocity signals representative of measured velocities of blood flow in the intracranial segment and extracranial segment, respectively, of the ophthalmic artery;
   a device for applying an external pressure against said eye and measuring and storing the applied external pressure;
   a processor adapted to calculate intracranial and extracranial angle-independent blood flow factors from said intracranial velocity signals and extracranial velocity signals and identify the absolute value of the intracranial pressure as that external pressure which causes the ratio of the intracranial angle-independent blood flow factor and the extracranial angle-independent blood flow factor to be equal to 1.

2. The apparatus of claim 1 wherein said Doppler device comprises an ultrasonic transducer.

3. The apparatus of claim 2 wherein said ultrasonic transducer comprises a 1D transducer array.

4. The apparatus of claim 2 wherein said ultrasonic transducer comprises a 2D transducer array.

5. The apparatus of claim 3 wherein said transducer can be manually rotated about its central axis so that said ultrasonic pulses can be directed at a plurality planes passing through a central axis of the transducer.

6. The apparatus of claim 1 wherein said Doppler device operates in either a scan mode or a spectral mode.

7. The apparatus of claim 1 wherein said scan-mode processing unit further comprises a colormap unit for generating a spatial 3D image of an intensity distribution of said Doppler signal.

8. The apparatus of claim 7 wherein said spatial 3D image is a color image wherein a colored Doppler signal is plotted against transducer steering angle and depth.

9. The apparatus of claim 1 wherein said spectral-mode processing unit concurrently measures the velocities of the blood flow in the intracranial segment and extracranial segment, respectively, of the ophthalmic artery, as identified by the intracranial and extracranial steering vectors.

10. The apparatus of claim 1 wherein said spectral-mode processing unit comprises a velocity spectrogram calculation unit for generating a intracranial velocity spectrogram from said intracranial velocity signal and an extracranial velocity spectrogram from said extracranial velocity signal.

11. The apparatus of claim 1 further comprising a pulse-wave spectrogram processing unit for generating a peak intracranial velocity envelope from said intracranial velocity signal and a peak extracranial velocity envelope from said extracranial velocity signal.

12. The apparatus of claim 11 wherein said device for identifying the intracranial pressure receives said peak intracranial velocity envelope and said peak extracranial velocity envelope and measures intracranial blood flow pulsation parameters and extracranial blood flow pulsation parameters therefrom.

13. The apparatus of claim 12 wherein said intracranial blood flow pulsation parameters and extracranial blood flow pulsation parameters comprise at least two measurement points on the peak intracranial velocity envelope and at least two measurement points on the peak extracranial velocity envelope, respectively, within one heart cycle.

14. The apparatus of claim 12 wherein said device for identifying the intracranial pressure further calculates an angle-independent intracranial blood flow factor and an angle-independent extracranial blood flow factor from the intracranial blood flow pulsation parameters and extracranial blood flow pulsation parameters.

15. The apparatus of claim 14 wherein said angle-independent intracranial blood flow factor and angle-independent extracranial blood flow factor are intracranial resistivity index and extracranial resistivity index, respectively.

16. The apparatus of claim 14 wherein said angle-independent intracranial blood flow factor and angle-independent extracranial blood flow factor are intracranial pulsatility index ($PI_{IOA}$) and extracranial pulsatility index ($PI_{EOA}$), respectively.

17. The apparatus of claim 16 wherein said intracranial blood flow pulsation parameters are intracranial peak systolic velocity ($VS_{IOA}$) and intracranial end diastolic velocity ($VS_{IOA}$) and said extracranial blood flow pulsation parameters are extracranial peak systolic velocity ($VS_{EOA}$) and extracranial end diastolic velocity ($VS_{EOA}$).

18. The apparatus of claim 17 wherein said intracranial pulsatility index ($PI_{IOA}$) and extracranial pulsatility index ($PI_{EOA}$) are calculated from the formulas:

$$PI_{IOA}=2*(VS_{IOA}-VD_{IOA})/(VS_{IOA}+VD_{IOA})$$

$$PI_{EOA}=2*(VS_{EOA}-VD_{EOA})/(VS_{EOA}+VD_{EOA}).$$

19. The apparatus of claim 18 wherein the absolute value of intracranial pressure is identified as that extracranial pressure which causes $PI_{IOA}$ to be equal to $PI_{EOA}$ or the ratio of $PI_{IOA}$ to $PI_{EOA}$ to be equal to 1.

20. A method for non-invasively determining the absolute value of intracranial pressure of a living body comprising the steps of:
   A. provide a Doppler device for noninvasively sensing the blood flow in an ophthalmic artery extending from inside the cranium into an eye of the living body;
   B. noninvasively locate an intracranial segment and extracranial segment of an ophthalmic artery extending from inside the cranium into the eye by steering the Doppler device to measure the velocity of blood flow at a plurality of depths and steering angles within a plurality of spatial planes passing through a central axis of the Doppler device and generate a Doppler signal representative of said measured blood flow velocities;
   C. apply an external pressure against said eye and measuring and storing the applied external pressure;
   D. concurrently generate intracranial velocity and extracranial velocity signals representative of measured velocities of the blood flow in the intracranial segment and extracranial segment of the ophthalmic artery, respectively, for an applied external pressure;
   E. generate an intracranial velocity spectrogram from said intracranial velocity signal and an extracranial velocity spectrogram from said extracranial velocity signal; and
   F. separate said intracranial velocity spectrogram and said extracranial velocity spectrogram into separate heart cycle spectrograms for individual heart cycles, aligning said heart cycle spectrograms for each heart cycle by cross-correlation, and calculating a peak intracranial velocity envelope and a peak extracranial velocity envelope.

21. The method of claim 20 further comprising a step of generating a spatial 3D image of an intensity distribution of said Doppler signal-plotted against steering angle and depth.

22. The method of claim 21 further comprising a step of placing a cursor on said spatial 3D image to select an intracranial steering parameter representative of a steering angle and a depth of the intracranial segment of the ophthalmic artery and placing a cursor on said spatial 3D image to select an extracranial steering parameter representative of the extracranial segment of the ophthalmic artery.

23. The method of claim 20 wherein said peak intracranial and extracranial velocity envelopes are calculated by generating a spectral envelope for each individual heart cycle spectrogram and averaging the spectral envelopes of the individual heart cycle spectrograms.

24. The method of claim 20 wherein said peak intracranial and extracranial velocity envelopes are calculated by averaging the individual heart cycle spectrograms and generating a spectral envelope from the average heart cycle spectrogram.

25. The method of claim 20 further comprising the step of measuring intracranial blood flow pulsation parameters and extracranial blood flow pulsation parameters from the peak intracranial and extracranial velocity envelopes, respectively.

26. The method of claim 25 wherein said intracranial blood flow pulsation parameters and extracranial blood flow pulsation parameters comprise at least two measurement points on the peak intracranial velocity envelope and at least two measurement points on the peak extracranial velocity envelope, respectively, within one heart cycle.

27. The method of claim 25 further comprising a step of calculating an angle-independent intracranial blood flow factor and angle-independent extracranial blood flow factor from the intracranial blood flow pulsation parameters and extracranial blood flow pulsation parameters.

28. The method of claim 27 further comprising steps of:
calculating the ratio of the angle-independent intracranial blood flow factor to the angle-independent extracranial blood flow factor;
if said ratio is not equal to 1, increase said applied extracranial pressure;
repeat steps A-D.

29. The method of claim 28 further comprising a step of identifying the absolute value of the intracranial pressure as that extracranial pressure which causes the angle-independent intracranial blood flow factor to be equal to the angle-independent extracranial blood flow factor or the ratio of the angle-independent intracranial blood flow factor to the angle-independent extracranial blood flow factor to be equal to 1.

30. The method of claim 29 wherein said angle-independent intracranial blood flow factor and angle-independent extracranial blood flow factor are intracranial resistivity index and extracranial resistivity index, respectively.

31. The method of claim 29 wherein said angle-independent intracranial blood flow factor and angle-independent extracranial blood flow factor are intracranial pulsatility index ($PI_{IOA}$) and extracranial pulsatility index ($PI_{EOA}$), respectively.

32. The method of claim 31 wherein said intracranial blood flow pulsation parameters are intracranial peak systolic velocity ($VS_{IOA}$) and intracranial end diastolic velocity ($VS_{IOA}$) and said extracranial blood flow pulsation parameters are extracranial peak systolic velocity ($VS_{EOA}$) and extracranial end diastolic velocity ($VS_{EOA}$).

33. The method of claim 32 wherein intracranial pulsatility index ($PI_{IOA}$) and extracranial pulsatility index ($PI_{EOA}$), are calculated from the formulas:

$$PI_{IOA}=2*(VS_{IOA}-VD_{IOA})/(VS_{IOA}+VD_{IOA})$$

$$PI_{EOA}=2*(VS_{EOA}-VD_{EOA})/(VS_{EOA}+VD_{EOA}).$$

34. An apparatus for non-invasively determining the absolute value of intracranial pressure of a living body comprising:
a device for noninvasively generating intracranial velocity and extracranial velocity signals representative of measured velocities of blood flow in an intracranial segment and extracranial segment, respectively of an ophthalmic artery extending from inside the cranium into an eye of the living body;
a device for applying an external pressure against said eye and measuring and storing the applied external pressure;
a processing unit adapted to:
generate an intracranial velocity spectrogram from said intracranial velocity signal and an extracranial velocity spectrogram from said extracranial velocity signal, separate said intracranial velocity spectrogram and said extracranial velocity spectrogram into separate heart cycle spectrograms for individual heart cycles, aligning said heart cycle spectrograms for each heart cycle by cross-correlation, and calculating a maximum intracranial velocity envelope and a maximum extracranial velocity envelope,
measure intracranial blood flow pulsation parameters and extracranial blood flow pulsation parameters from the maximum intracranial and extracranial velocity envelopes, respectively;
calculate intracranial and extracranial angle-independent blood flow factors from said intracranial blood flow pulsation parameters and extracranial blood flow pulsation parameters; and
identify the absolute value of the intracranial pressure as that extracranial pressure which causes the ratio of the intracranial angle-independent blood flow factor to the extracranial angle-independent blood flow factor to be equal to 1.

35. The apparatus of claim 34 wherein said maximum intracranial and extracranial velocity envelopes are calculated by generating a spectral envelope for each individual heart cycle spectrogram and averaging the spectral envelopes of the individual heart cycle spectrograms.

36. The apparatus of claim 35 wherein said maximum intracranial and extracranial velocity envelopes are calculated by averaging the individual heart cycle spectrograms and generating a spectral envelope from the average heart cycle spectrogram.

37. The apparatus of claim 34 wherein said intracranial blood flow pulsation parameters are intracranial peak systolic velocity ($VS_{IOA}$) and intracranial end diastolic velocity ($VS_{IOA}$) and said extracranial blood flow pulsation parameters are extracranial peak systolic velocity ($VS_{EOA}$) and extracranial end diastolic velocity ($VS_{EOA}$).

38. The apparatus of claim 37 wherein said intracranial and extracranial angle-independent blood flow factors are intracranial pulsatility index ($PI_{IOA}$) and extracranial pulsatility index ($PI_{EOA}$), respectively.

39. The apparatus of claim 38 wherein said intracranial pulsatility index ($PI_{IOA}$) and extracranial pulsatility index ($PI_{EOA}$) are calculated from the formulas:

$$PI_{IOA}=2*(VS_{IOA}-VD_{IOA})/(VS_{IOA}+VD_{IOA})$$

$$PI_{EOA}=2*(VS_{EOA}-VD_{EOA})/(VS_{EOA}+VD_{EOA}).$$

* * * * *